United States Patent
Haque et al.

(10) Patent No.: US 7,933,438 B2
(45) Date of Patent: Apr. 26, 2011

(54) MAXIMUM INTENSITY PROJECTION PERFORMING METHOD AND APPARATUS

(75) Inventors: Hasnine A. Haque, Tokyo (JP); Bilgin Keserci, Tokyo (JP)

(73) Assignee: GE Medical Systems Global Technology Company, LLC, Waukesha, WI (US)

(*) Notice: Subject to any disclaimer, the term of this patent is extended or adjusted under 35 U.S.C. 154(b) by 961 days.

(21) Appl. No.: 11/691,681

(22) Filed: Mar. 27, 2007

(65) Prior Publication Data

US 2007/0237379 A1    Oct. 11, 2007

(30) Foreign Application Priority Data

Apr. 6, 2006  (JP) .................................. 2006-104970

(51) Int. Cl.
*G06K 9/00* (2006.01)
(52) U.S. Cl. .................................. 382/130; 382/154
(58) Field of Classification Search .................. 382/130, 382/154
See application file for complete search history.

(56) References Cited

U.S. PATENT DOCUMENTS

| 5,297,551 | A | * | 3/1994 | Margosian et al. ........... 600/410 |
| 5,368,033 | A | * | 11/1994 | Moshfeghi ................... 600/419 |
| 5,802,133 | A | * | 9/1998 | Kawai et al. |
| 5,818,896 | A | * | 10/1998 | Hsieh ........................... 378/15 |
| 6,211,674 | B1 | | 4/2001 | Cline et al. |
| 7,020,318 | B2 | * | 3/2006 | Oshio et al. ................... 382/131 |
| 7,250,949 | B2 | * | 7/2007 | Claus et al. ................... 345/424 |
| 7,583,779 | B2 | * | 9/2009 | Tkaczyk et al. ................ 378/4 |
| 2005/0134582 | A1 | * | 6/2005 | Claus et al. |
| 2006/0020202 | A1 | * | 1/2006 | Mathew et al. |

FOREIGN PATENT DOCUMENTS

| EP | 0621546 A | * | 10/1994 |
| JP | 11-056840 | | 3/1999 |

OTHER PUBLICATIONS

Heidrich et al. "Interactive Maximum Projection Volume Rendering" In Proceedings Visualization 1995.*
Octrooicentrum Nederland Onderzoeksrapport (Netherland Search Report) for NL1033651 dated Sep. 21, 2007.

* cited by examiner

*Primary Examiner* — Bhavesh M Mehta
*Assistant Examiner* — Utpal Shah
(74) *Attorney, Agent, or Firm* — Armstrong Teasdale LLP

(57) ABSTRACT

In order to visualize a narrow blood vessel overlapping a thick blood vessel, at the time of performing a maximum intensity projection on three-dimensional image data, three-dimensional image data is weighted with a plurality of weighting functions of different attenuation characteristics along a projection line. Maximum intensity projections are performed on the plurality of pieces of the weighted three-dimensional image data, and results of all of the maximum intensity projections are summed. The weight of the weighting function is zero until the projection line reaches the surface of an image and, after the reach, gradually decreases from an initial value. Alternatively, the weight of the weighting function is zero to some midpoint of the projection line and, after the midpoint, gradually decreases from the initial value. The midpoint is adjustable. The attenuation characteristic is given by an exponential function. Parameters of the exponential function are adjustable.

20 Claims, 3 Drawing Sheets

US 7,933,438 B2

MAXIMUM INTENSITY PROJECTION PERFORMING METHOD AND APPARATUS

CROSS REFERENCE TO RELATED APPLICATIONS

This application claims the benefit of Japanese Application No. 2006-104970 filed Apr. 6, 2006.

BACKGROUND OF THE INVENTION

The present invention relates to a maximum intensity projection (MIP) performing method and apparatus and, more particularly, to a method and apparatus for performing a maximum intensity projection on three-dimensional image data.

In the case of imaging an extending state of blood vessels in a body, a maximum intensity projection on three-dimensional image data captured by angiography or the like is performed. The maximum intensity projection is performed by extracting the maximum image data encountered by a projection line passing a data space on a projection line unit basis. The maximum intensity projection is also called MIP. The image obtained by the maximum intensity projection is also called an MIP image (refer to, for example, Japanese Patent Laid-Open No. Hei 11(1999)-056840).

An MIP image does not have depth information. Therefore, the relations of blood vessels in depth are not clearly seen and it is difficult to grasp the blood vessel extending state in depth. A narrow blood vessel overlapping a thick blood vessel cannot be visualized in any of the forward and back directions of projection (forward and back projections).

To address such a problem, a plurality of MIP images are captured while shifting the projection direction little by little and are displayed like a moving picture. However, it is inconvenient to capture a number of MIP images in different projection directions.

SUMMARY OF THE INVENTION

An object of the present invention is, therefore, to realize a maximum intensity projection performing method and apparatus capable of capturing images in perspective. Another object of the invention is to realize a maximum intensity projection performing method and apparatus capable of visualizing a narrow blood vessel overlapping a thick blood vessel.

The present invention according to an aspect for solving the problem provides a maximum intensity projection method for performing a maximum intensity projection on three-dimensional image data, comprising the steps of: assigning weights to three-dimensional image data with a plurality of weighting functions having different attenuation characteristics along a projection line; performing maximum intensity projections on the weighted three-dimensional image data; and summing results of all of the maximum intensity projections.

The invention according to another aspect for solving the problem provides a maximum intensity projection performing apparatus for performing a maximum intensity projection on three-dimensional image data, including: weight assigning means for assigning weights to three-dimensional image data with a plurality of weighting functions having different attenuation characteristics along a projection line; maximum intensity projection performing means for performing maximum intensity projections on the weighted three-dimensional image data; and summing means for summing results of all of the maximum intensity projections.

To effectively assign weights, preferably, the weight of the weighting function is zero until a projection line reaches an image surface and, after the reach, the weight gradually decreases from an initial value.

To effectively assign weights, preferably, the weight of the weighting function is zero until some midpoint of the projection line and, after the midpoint, gradually decreases from an initial value.

To visualize a narrow blood vessel hidden by a thick blood vessel, preferably, the midpoint is adjustable.

To properly perform attenuation, preferably, the attenuation characteristic is given by the sum of an exponential function and a constant.

To assign weights properly, preferably, parameters of the exponential function and the constant are adjustable.

To minimize the weighting functions, preferably, the plurality of weighting functions are two weighting functions.

To obtain a global maximum and a local maximum, preferably, attenuation of one of the two weighting functions is relatively gentle, and that of the other weighting function is relatively sharp.

To properly obtain a global maximum and a local maximum, preferably, an initial value of one of the two weighting functions is relatively large, and that of the other weighting function is relatively small.

To capture an MIP image of a coronary artery, preferably, the three-dimensional image data is image data of a heart on which angiography is performed.

The invention according to each of the aspects can realize a maximum intensity projection performing method and apparatus capable of obtaining an image in perspective, in which at the time of performing a maximum intensity projection on three-dimensional image data, weights are assigned to three-dimensional image data with a plurality of weighting functions having different attenuation characteristics along a projection line, maximum intensity projections are performed on the weighted three-dimensional image data, and results of all of the maximum intensity projections are summed. The invention can also realize a maximum intensity projection performing method and apparatus capable of visualizing a narrow blood vessel overlapping a thick blood vessel.

Further objects and advantages of the present invention will be apparent from the following description of the preferred embodiments of the invention as illustrated in the accompanying drawings.

DETAILED DESCRIPTION OF THE INVENTION

Figure 1:
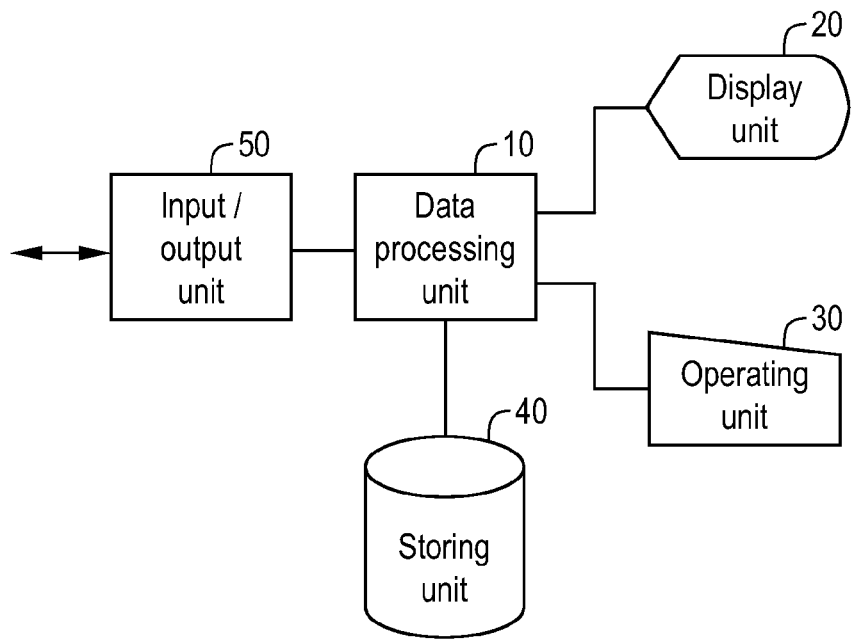
FIG. 1 is a diagram showing the configuration of an image processing apparatus as an example of the best mode for carrying out the invention.

A best mode for carrying out the present invention will be described hereinbelow with reference to the drawings. The present invention is not limited to the best mode for carrying out the invention. FIG. 1 is a block diagram showing the configuration of an image processing apparatus.

The apparatus is an example of the best mode for carrying out the invention. By the configuration of the apparatus, an example of the best mode for carrying out the invention related to a maximum intensity projection performing apparatus is shown. By the operation of the apparatus, an example of the best mode for carrying out the invention related to a maximum intensity projection performing method is shown.

As shown in FIG. 1, the apparatus has a data processing unit 10, a display unit 20, an operating unit 30, a storing unit 40, and an input/output unit 50.

The data processing unit 10 performs a predetermined data process on data stored in the storing unit 40 on the basis of an interactive operation of the user via the display unit 20 and the operating unit 30.

The data processing unit 10 inputs/outputs data from/to an external apparatus via the input/output unit 50. An image to be subjected to a maximum intensity projection is also input from an external apparatus via the input/output unit 50. The external apparatus is, for example, a medical imaging apparatus such as an X-ray CT apparatus or an MRI apparatus or a medical image server. The apparatus may be part of a medical imaging apparatus or a medical image server. In this case, the input/output unit 50 is not always necessary.

The maximum intensity projection will be described. The maximum intensity projection is performed by the data processing unit 10. The data processing unit 10 captures a maximum intensity projection image by the following expression.

$$iMIP(y,z)=S_1+S_2+\ldots S_m \text{ for } z=1\ldots N_z, y=1\ldots N_y \quad \text{(Expression 1)}$$

As shown in the expression, a maximum intensity projection image iMIP(y, z) is obtained by the sum of m pieces of images S1, S2, ..., and Sm. The images S1, S2, ..., and Sm are given by the following expressions.

$$S_1(y,z)=\text{Max}[I(x,y,z)*w_1(x-\alpha(y,z))]_{x=\alpha\ldots Nx}$$

$$S_2(y,z)=\text{Max}[I(x,y,z)*w_2(x-\alpha(y,z))]_{x=\alpha\ldots Nx}$$

$$S_m(y,z)=\text{Max}[I(x,y,z)*w_m(x-\alpha(y,z))]_{x=\alpha\ldots Nx} \quad \text{(Expressions 2)}$$

As shown in the expressions, an image Si (i=1, 2, ..., and m) is captured by performing the maximum intensity projection (MIP) on a value obtained by multiplying three-dimensional image data I(x, y, z) with a weighting function wi(x−α). The direction of a projection line is the x direction. The matrix size of the three-dimensional image I(x, y, z) is Nx*Ny*Nz. By multiplying I(x, y, z) with rotation matrix, a maximum intensity projection image from an arbitrary direction can be obtained. A weighting function wm(x) is given by the following expression.

$$W_m(x)=a_m+C_m\exp^{[-(x-\alpha(y,z))/b^m]} \text{ for } x>=\alpha(y,z)$$

$$W_m(x)=0 \text{ for } x<\alpha(y,z) \quad \text{(Expression 3)}$$

As shown in the expression, in the weighting function wm(x), weight is 0 in the range of x<α and attenuates exponentially in the range of x>α. α(y, z) is a distance from a departure point of a projection line to the image surface and is a value which varies depending on (y, z). When x=α, the weighting function has the initial value.

In parameters am, bm, and cm of the weighting function, cm denotes an initial value adjusting coefficient, am denotes a bias of the weight, and bm denotes an attenuation coefficient. Each of the parameters can be adjusted by the user.

Figure 2:
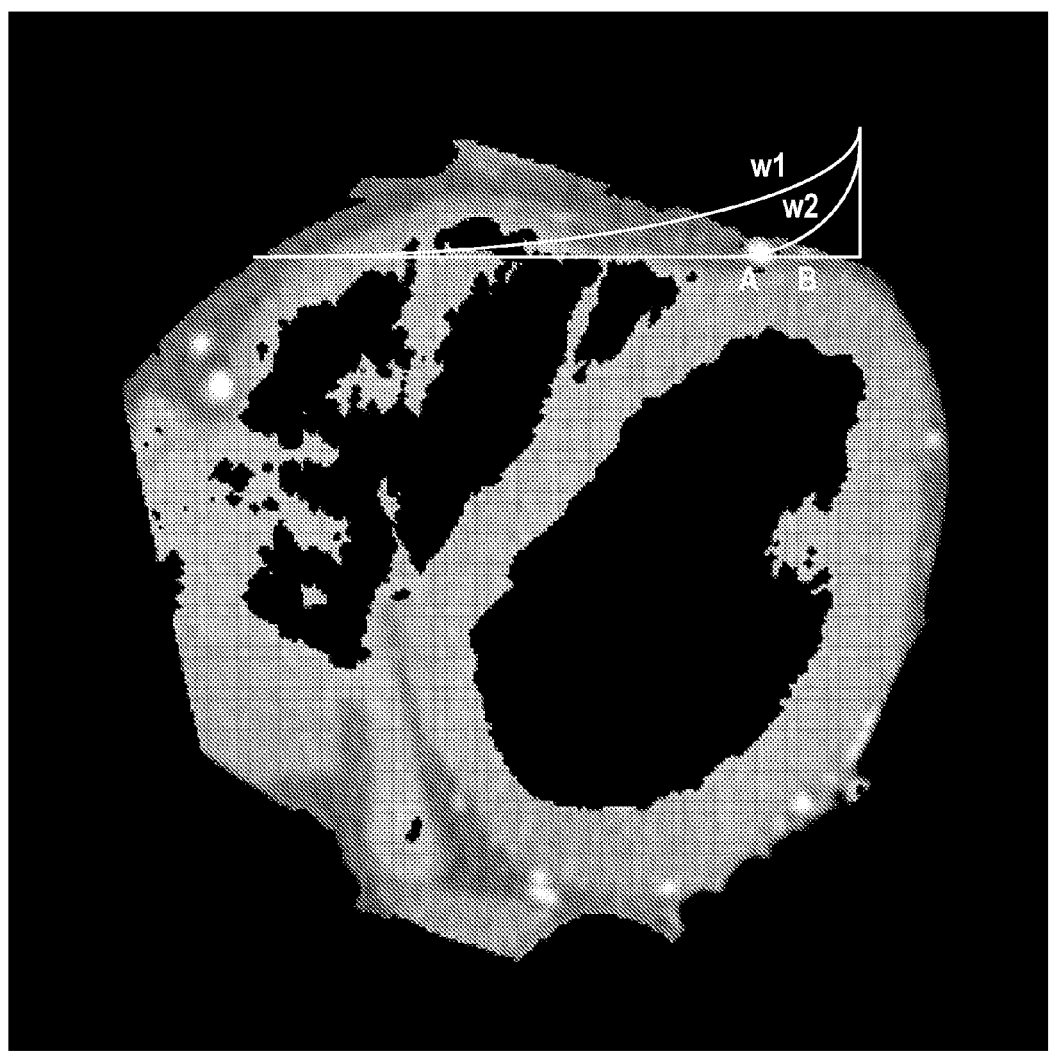
FIG. 2 is a diagram of a half-tone picture of a slice image of a heart captured with a contrast medium.

FIG. 2 shows an example of weighting functions and a slice image of a heart to which the weighting functions are applied. The slice image of a heart is captured by contrast image capturing. Blood vessel portions have high brightness. As the weighting functions, two kinds of weighting functions w1 and w2 are used.

In the weighting function w1, weight attenuates in a wide range on a projection line. In the weighting function w2, weight attenuates in a narrow range on a projection line. The attenuation characteristic of the weighting function w1 is relatively gentle, and that of the weighting function w2 is relatively sharp. The initial value of the weight of the weighting function w1 is relatively large, and that of the weighting function w2 is relatively small.

The weighting function w1 is suitable for performing the maximum intensity projection at a global maximum. The weighting function w2 is suitable for performing the maximum intensity projection at a local maximum.

By applying the weighting functions to a slice image of the heart, an image in which brightness gradually decreases from right to left as shown by an inserted image at the left corner is captured. This is because the weight gradually decreases from right to left. Since the weight degreases from the surface (x=α) of an image as a start point, decrease in brightness also starts from the surface of the heart.

α may not be set as the distance to the surface of an image but may be a proper distance to be set by the user. When α is set by the user, the start point of the decrease in weight, that is, the position corresponding to the initial value of the weight can be adjusted to the position of a target blood vessel. It enables a target blood vessel to be visualized with high visibility.

Figure 3:
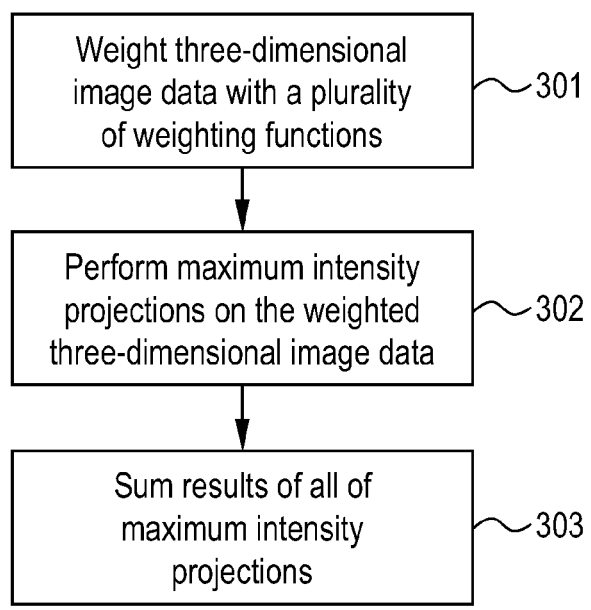
FIG. 3 is a diagram showing processes for capturing a maximum intensity projection image.

FIG. 3 shows processes for obtaining a maximum intensity projection image. As shown in FIG. 3, the maximum intensity projection is performed by three processes 301, 302, and 303. The processes are performed by the data processing unit 10.

In the process 301, three-dimensional image data is weighted with a plurality of weighting functions. The three-dimensional image data is I(x, y, z). The plurality of weighting functions are w1(x), w2(x), ..., and wm(x). The data processing unit 10 for executing the process 301 is an example of weighting means in the present invention.

In the process 302, a maximum intensity projection is performed on each piece of the weighted three-dimensional image data, thereby obtaining a plurality of images S1(y, z), S2(y, z), ..., and Sm(y, z). The data processing unit 10 for executing the process 302 is an example of the maximum intensity projection performing means in the present invention.

In the process 303, results of all of the maximum intensity projections are summed. By the process, the images S1, S2, ..., and Sm are summed. Specifically, the sum of the images S1, S2, ..., and Sm is obtained and the maximum intensity projection image iMIP is captured. The data processing unit 10 for executing the process 303 is an example of summing means in the present invention.

Figure 4A:
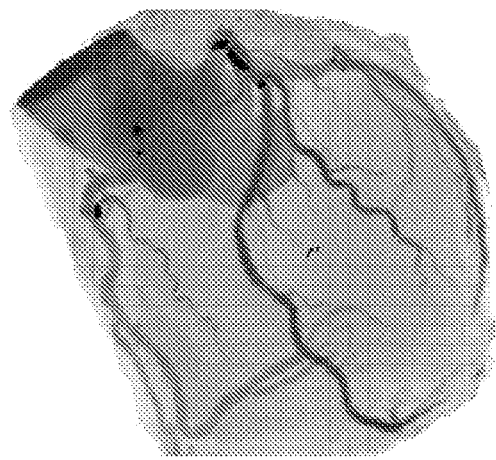
FIGS. 4A to 4C are diagrams of half-tone pictures of maximum intensity projection images of the heart.
Figure 4B:
Figure 4C:
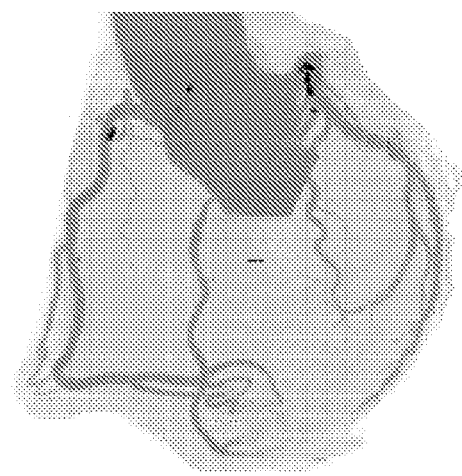

FIGS. 4A to 4C show actual examples of the maximum intensity projection image iMIP in comparison with a maximum intensity projection image captured by the conventional method. FIGS. 4A and 4B show the maximum intensity projection images iMIP and FIG. 4C shows the maximum intensity projection image iMIP captured by the conventional method.

As obvious from FIGS. 4A to 4C, the maximum intensity projection images iMIP have depth information and the maximum intensity projection image captured by the conventional method is an image which does not have depth information. Therefore, in the maximum intensity projection image iMIP, the positional relations of the blood vessels in depth are clear, and blood vessels in depth can be easily grasped. Moreover, a narrow blood vessel overlapping a thick blood vessel is also clearly visualized. Consequently, the state of a coronary artery in three dimensions can be recognized.

Since the weight of the weighting function is zero until the projection line reaches the image surface and, after the projection line reaches the image surface, the weight gradually degreases from the initial value, the shape of the heart is clearly visualized in the maximum intensity projection image iMIP and the background of the blood vessel image is uniform.

Although an example of a maximum intensity projection image of the heart captured by angiography has been described above, the method of the invention is not limited to the example but can be widely applied to capture maximum intensity projection images of various targets to be captured. Although the example of giving the attenuation characteristic of a weighting function by an exponential function has been described above, the invention is not limited to the attenuation characteristic given by an exponential function but may be a proper attenuation characteristic.

Many widely different embodiments of the invention may be configured without departing from the spirit and the scope of the present invention. It should be understood that the present invention is not limited to the specific embodiments described in the specification, except as defined in the appended claims.

The invention claimed is:

1. A maximum intensity projection performing method for performing a maximum intensity projection on three-dimensional image data, said method comprising:
    assigning weights to three-dimensional image data using a plurality of weighting functions having different attenuation characteristics along a projection line to generate a plurality of weighted three-dimensional image data pieces;
    performing a maximum intensity projection on each of the plurality of weighted three-dimensional image data pieces; and
    summing results of all of the maximum intensity projections of the plurality of weighted three-dimensional image data pieces.

2. The maximum intensity projection performing method according to claim 1, wherein the weight of the weighting function is zero until a projection line reaches an image surface and, after the projection line reaches the image surface, the weight gradually decreases from an initial value.

3. The maximum intensity projection performing method according to claim 1, wherein the weight of the weighting function is zero until a midpoint of the projection line and, after the midpoint, the weight gradually decreases from the initial value.

4. The maximum intensity projection performing method according to claim 3, wherein the midpoint is adjustable.

5. The maximum intensity projection performing method according to claim 1, wherein the attenuation characteristic is given by the sum of an exponential function and a constant.

6. The maximum intensity projection performing method according to claim 5, wherein parameters of the exponential function and the constant are adjustable.

7. The maximum intensity projection performing method according to claim 1, wherein the plurality of weighting functions are two weighting functions.

8. The maximum intensity projection performing method according to claim 7, wherein one of the two weighting functions attenuates more gradually than the other weighting function.

9. The maximum intensity projection performing method according to claim 7, wherein an initial value of one of the two weighting functions is larger than that of the other weighting function.

10. The maximum intensity projection performing method according to claim 1, wherein the three-dimensional image data is image data of a heart on which angiography is performed.

11. A maximum intensity projection performing apparatus for performing a maximum intensity projection on three-dimensional image data, comprising:
    a weight assigning device for assigning weights to three-dimensional image data with a plurality of weighting functions having different attenuation characteristics along a projection line, said weight assigning device capable of generating a plurality of weighted three-dimensional image data pieces;
    a maximum intensity projection performing device for performing maximum intensity projections on each of the plurality of weighted three-dimensional image data pieces; and
    a summing device for summing results of all of the maximum intensity projections of the plurality of weighted three-dimensional image data pieces.

12. The maximum intensity projection performing apparatus according to claim 11, wherein the weight of the weighting function is zero until a projection line reaches an image surface and, after the projection line reaches the image surface, the weight gradually decreases from an initial value.

13. The maximum intensity projection performing apparatus according to claim 11, wherein the weight of the weighting function is zero until a midpoint of the projection line and, after the midpoint, the weight gradually decreases from an initial value.

14. The maximum intensity projection performing apparatus according to claim 13, wherein the midpoint is adjustable.

15. The maximum intensity projection performing apparatus according to claim 11, wherein the attenuation characteristic is given by the sum of an exponential function and a constant.

16. The maximum intensity projection performing apparatus according to claim 15, wherein parameters of the exponential function and the constant are adjustable.

17. The maximum intensity projection performing apparatus according to claim 11, wherein the plurality of weighting functions are two weighting functions.

18. The maximum intensity projection performing apparatus according to claim 17, wherein one of the two weighting functions attenuates more gradually than the other weighting function.

19. The maximum intensity projection performing apparatus according to claim 17, wherein an initial value of one of the two weighting functions is larger than that of the other weighting function.

20. The maximum intensity projection performing apparatus according to claim 11, wherein the three-dimensional image data is three-dimensional image data of a heart on which angiography is performed.

* * * * *